(12) United States Patent
Krueger et al.

(10) Patent No.: US 8,573,071 B2
(45) Date of Patent: Nov. 5, 2013

(54) HEATING, SHAKING, AND MAGNETIZING APPARATUS AND METHOD OF OPERATING THE SAME

(75) Inventors: Steve Krueger, Deerfield, WI (US);
Julia E. Krueger, Deerfield, WI (US);
Cristopher Cowan, Fitchburg, WI (US);
Aaron Bonk, Reno, NV (US)

(73) Assignee: Promega Corporation, Madison, WI (US)

( * ) Notice: Subject to any disclaimer, the term of this patent is extended or adjusted under 35 U.S.C. 154(b) by 393 days.

(21) Appl. No.: 12/905,229

(22) Filed: Oct. 15, 2010

(65) Prior Publication Data

US 2011/0088491 A1    Apr. 21, 2011

Related U.S. Application Data

(60) Provisional application No. 61/252,390, filed on Oct. 16, 2009.

(51) Int. Cl.
*G01N 1/22* (2006.01)
*B01D 21/00* (2006.01)

(52) U.S. Cl.
USPC ........................ 73/863.11; 422/527

(58) Field of Classification Search
USPC ............... 73/863.11; 422/552, 560, 530, 427; 366/273, 274
See application file for complete search history.

(56) References Cited

U.S. PATENT DOCUMENTS

| | | | |
|---|---|---|---|
| 4,895,650 A | 1/1990 | Wang | 210/222 |
| 5,571,481 A * | 11/1996 | Powell et al. | 422/562 |
| 6,033,574 A | 3/2000 | Siddiqi | 210/695 |
| 6,117,398 A | 9/2000 | Bienhaus et al. | 422/527 |
| 6,228,268 B1 | 5/2001 | Siddiqi | 210/695 |
| 6,231,760 B1 | 5/2001 | Siddiqi | 210/222 |
| 6,500,343 B2 | 12/2002 | Siddiqi | 210/695 |
| 6,884,357 B2 | 4/2005 | Siddiqi | 210/695 |
| 7,267,800 B2 | 9/2007 | Takii et al. | 422/501 |
| 7,384,559 B2 | 6/2008 | a Brassard | 210/695 |
| 7,476,313 B2 | 1/2009 | Siddiqi | 210/695 |
| 7,517,457 B2 | 4/2009 | Siddiqi | 210/695 |
| 7,815,866 B2 * | 10/2010 | Safar et al. | 422/509 |
| 2002/0014443 A1 | 2/2002 | Hansen et al. | 209/213 |

(Continued)

FOREIGN PATENT DOCUMENTS

| | | |
|---|---|---|
| CN | 102596412 | 7/2012 |
| DE | 102008009920 | 8/2009 |

(Continued)

OTHER PUBLICATIONS

International Search Report and Written Opinion for Application No. PCT/US2010/052799 dated Jan. 27, 2011 (11 pages).

*Primary Examiner* — Peter Macchiarolo
*Assistant Examiner* — Tamiko Bellamy
(74) *Attorney, Agent, or Firm* — Michael Best & Friedrich LLP

(57) ABSTRACT

An apparatus for processing a liquid sample in a sample tube. The apparatus includes a base, a receptacle for receiving a sample tube, and a heating portion coupled to the base to selectively apply heat to the receptacle. A shaking portion is coupled to the base and supports the receptacle. The shaking portion agitates the receptacle with respect to the base. A magnetizing portion is coupled to the base and movable to selectively change a magnetic field with respect to the receptacle.

17 Claims, 12 Drawing Sheets

(56) References Cited

U.S. PATENT DOCUMENTS

| | | | |
|---|---|---|---|
| 2002/0098121 A1 | 7/2002 | Astle | 422/527 |
| 2003/0012699 A1 | 1/2003 | Moore et al. | 422/400 |
| 2005/0155921 A1 | 7/2005 | Siddiqi | 210/222 |
| 2007/0114181 A1 | 5/2007 | Li et al. | 210/695 |
| 2007/0221543 A1 | 9/2007 | Karmeniemi et al. | 209/223.1 |
| 2009/0173681 A1 | 7/2009 | Siddiqi | 210/222 |
| 2009/0211956 A1 | 8/2009 | Siddiqi | 210/138 |
| 2011/0091879 A1* | 4/2011 | Hillebrand et al. | 435/6 |
| 2012/0183441 A1* | 7/2012 | Schilffarth et al. | 422/82.05 |

FOREIGN PATENT DOCUMENTS

| | | |
|---|---|---|
| WO | 92/05443 | 4/1992 |
| WO | 99/57561 | 11/1999 |
| WO | 2008/057375 | 5/2008 |
| WO | 2011/047233 | 4/2011 |

* cited by examiner

HEATING, SHAKING, AND MAGNETIZING APPARATUS AND METHOD OF OPERATING THE SAME

CROSS-REFERENCE TO RELATED APPLICATIONS

This application claims priority to U.S. Provisional Patent Application No. 61/252,390, filed on Oct. 16, 2009, the content of which is incorporated herein by reference in its entirety.

BACKGROUND

The invention relates to laboratory sample processing equipment. More particularly, the invention relates to an apparatus for multi-step processing of blood and other liquid samples.

In the purification of biological molecules, such as DNA, from larger volumes of sample, there is a need to reduce processing time while increasing systematic reliability. In current practice, eight sample tubes are held in racks, and the racks are moved from a heating station to a magnet station to a shaker station many times during the course of processing a sample. One alternative to this method is the use of a large centrifuge. However, the downsides of the centrifuge method are potential cross contamination from open tubes, loss of pellets in dumping tubes, and the general reliability and liquid handling problems associated with the automatic addition and removal of tubes from a centrifuge.

SUMMARY

In one embodiment, the invention provides an apparatus for processing a liquid sample in a sample tube. The apparatus includes a base, a receptacle for receiving a sample tube, and a heating portion coupled to the base to selectively apply heat to the receptacle. A shaking portion is coupled to the base and supports the receptacle. The shaking portion selectively agitates the receptacle with respect to the base. A magnetizing portion is coupled to the base and movable to selectively change a magnetic field with respect to the receptacle.

In another embodiment, the invention provides a sample processing apparatus. The apparatus includes a base, a platform coupled to the base for motion with respect to the base, and a platform drive assembly. The platform drive assembly includes a platform drive motor coupled to the base and an orbital drive coupled to the platform. A receptacle is fixedly coupled to the platform. The receptacle receives a sample tube and includes a heating portion for selectively applying a heat to the sample tube. A magnetizing portion is movably coupled to the base. The magnetizing portion includes a permanent magnet having a first magnetic field orientation with respect to the receptacle and a second magnetic field orientation with respect to the receptacle. A magnet drive assembly is coupled to the platform and the magnetizing portion for moving the permanent magnet between the first magnetic field orientation and the second magnetic field orientation.

In yet another embodiment, the invention provides an apparatus for selectively heating, shaking, and magnetizing a plurality of sample tubes. The apparatus includes a base member, a drive assembly including a drive motor and an orbital shaker assembly coupled to the drive motor, and a heater block assembly coupled to the orbital shaker assembly for orbital motion with respect to the base member. The heater block assembly includes a heater block having a plurality of apertures for receiving a sample tube, and an electric heater thermally coupled to the heater block for applying a heat to the sample tubes. A magnet assembly includes a magnet having a magnetic field and a drive coupled to the base for moving the magnet between a first magnetic field orientation and a second magnetic field orientation. A controller selectively energizes the electric heater, selectively operates the drive assembly, and selectively moves the magnet between the first magnetic field orientation and the second magnetic field orientation.

In still yet another embodiment, the invention provides a method of heating, shaking, and magnetizing a plurality of samples supported by a plurality of respective sample tubes. The method is performed by an apparatus including a base, a shaking portion movably coupled to the base, the shaking portion including a heating portion and a plurality of receptacles for receiving the sample tubes, and a magnetizing portion coupled to the base. The magnetizing portion includes a plurality of magnets. The method includes receiving the plurality of sample tubes with the plurality of receptacles and heating the plurality of samples tubes with the heating portion. The magnetizing portion is rotated from a first position to a second position. The second position provides a substantial magnetic flux to the plurality of samples and the first position provides an insubstantial magnetic flux to the plurality of samples. The plurality of samples is magnetized with the plurality of magnets while the magnetizing portion is in the second position. The magnetizing portion is rotated from the second position to the first position. The plurality of sample tubes is shaken with the shaking portion while the magnetizing portion is in the first position.

Other aspects of the invention will become apparent by consideration of the detailed description and accompanying drawings.

BRIEF DESCRIPTION OF THE DRAWINGS

FIG. 7a is an exploded view of one heater block of the heater block assembly of FIG. 6.

FIG. 7b is an alternative perspective view of an aluminum core of the heater block of FIG. 7a.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
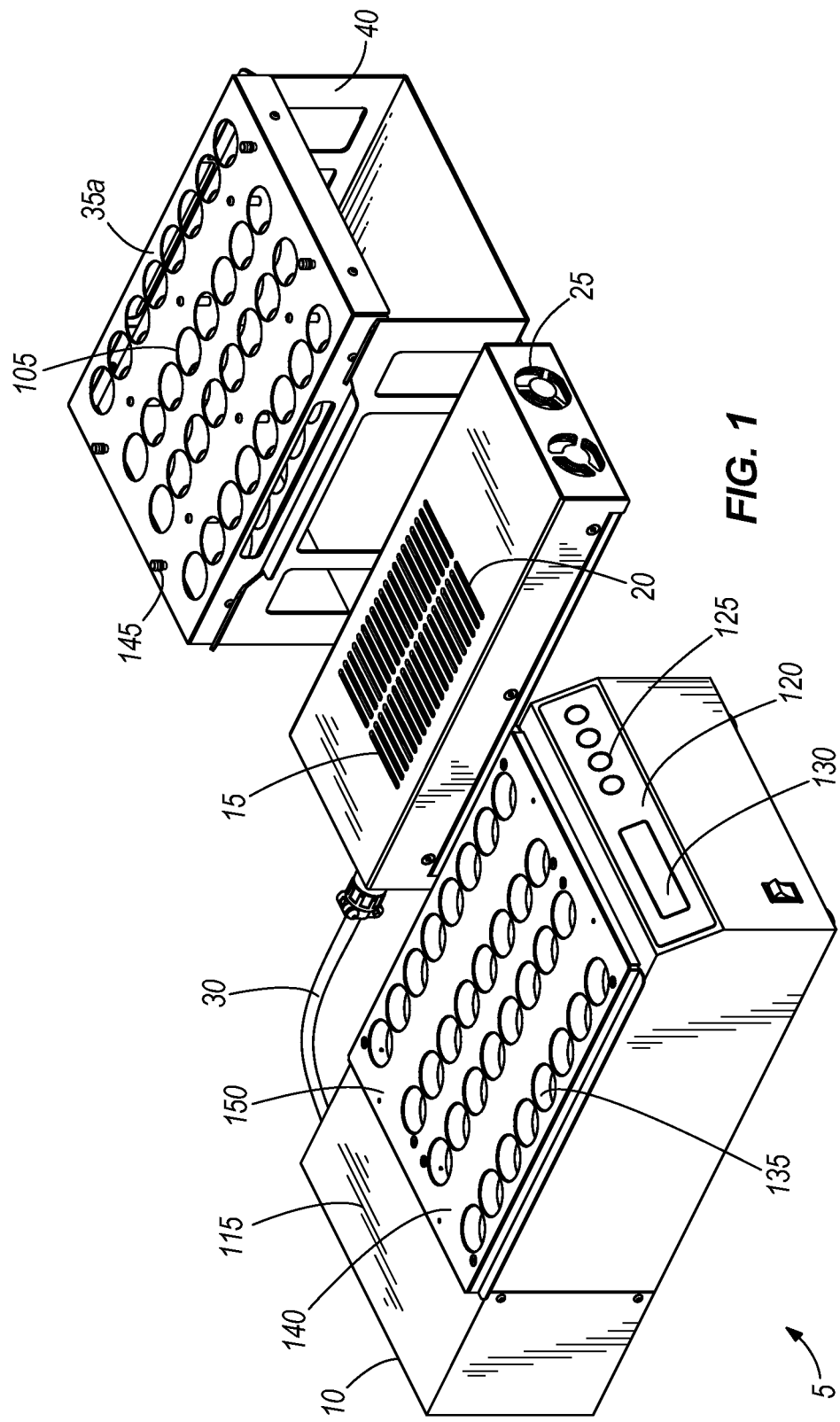
FIG. 1 is a perspective view of one embodiment of a heating, shaking, and magnetizing apparatus.

In one embodiment, the invention provides a heating, shaking, and magnetizing apparatus 5 for processing liquid samples. FIG. 1 is a perspective view of the apparatus 5, including a heater/shaker/magnetizer ("HSM") 10 device (or module) and associated support equipment. A conventional AC to DC power supply 15 connects to the HSM 10 for supplying a DC current at a desired voltage from an AC line supply. In the construction shown, the power supply 15 includes a plurality of ventilation louvers 20 and fan ports 25 for air cooling of the power supply 15. A cable 30 connects the power supply output to the HSM 10. In other constructions, the power supply 15 may be integrated within the HSM 10.

Figure 2A:
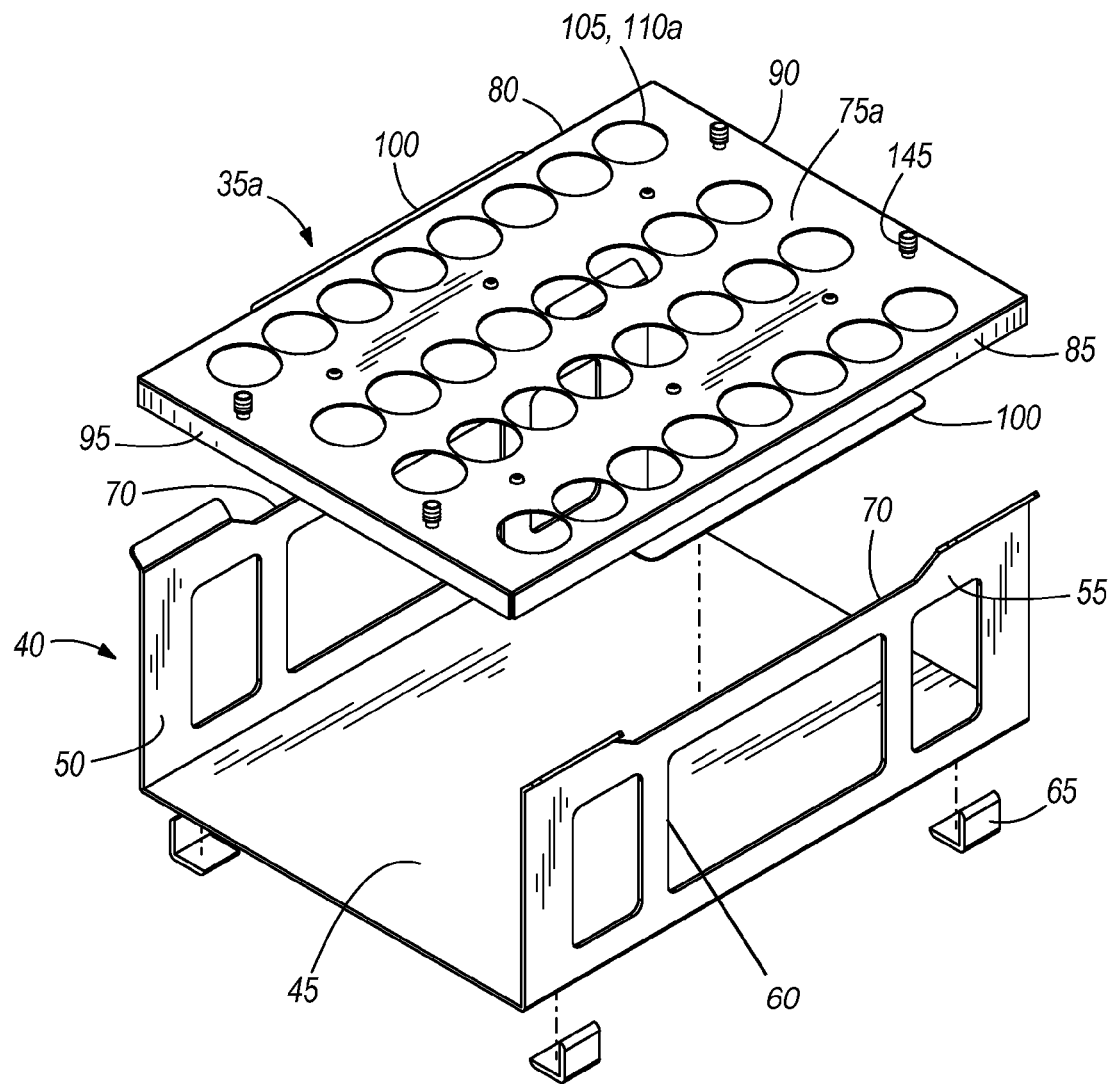
FIG. 2a is a perspective view of a transport rack and rack stand of FIG. 1

As shown in greater detail by FIG. 2a, a transport rack 35a and rack stand 40 is additionally provided. The rack stand 40 has a flat bottom portion 45 and first and second vertical risers 50, 55. In the construction shown, the bottom 45 and risers 50, 55 are integrally formed from a single piece of metal sheet stock. In other constructions, the rack stand 40 is formed from a variety of materials, including plastics and metals, and by a variety of means including injection molding, stamping, bending, and extrusion. As shown, the risers 50, 55 may have a plurality of cutout windows 60 formed therein. Rubber or plastic feet 65 are fixed to the bottom portion 45 to prevent the rack stand 40 from sliding and to raise the bottom portion 45 off of a laboratory table or other surface. Along the top edges of the first and second risers 50, 55, cutouts 70 are formed for receiving and holding the transport rack 35.

The transport rack 35a is a rectangular plane with a top surface 75a and four perpendicular edge surfaces 80, 85, 90, 95. Along first and second edge surfaces 80, 85, tab members 100 extend outwards laterally. The size of the tab members 100 is such that the tab members nest within the corresponding cutouts 70 of the first and second risers of the rack stand. The top surface 75a of the rack has a plurality of circular apertures 105 formed therein. The plurality of apertures forms an array 110a of columns and rows. The apertures 105 may be sized to receive and engage a surface of a container, such as a surface of a cylindrical or conical sample tube. In the construction shown, the apertures 105 are sized to receive and engage a 50 ml conical tube, such as for use in processing 10 ml samples of blood.

Figure 2B:
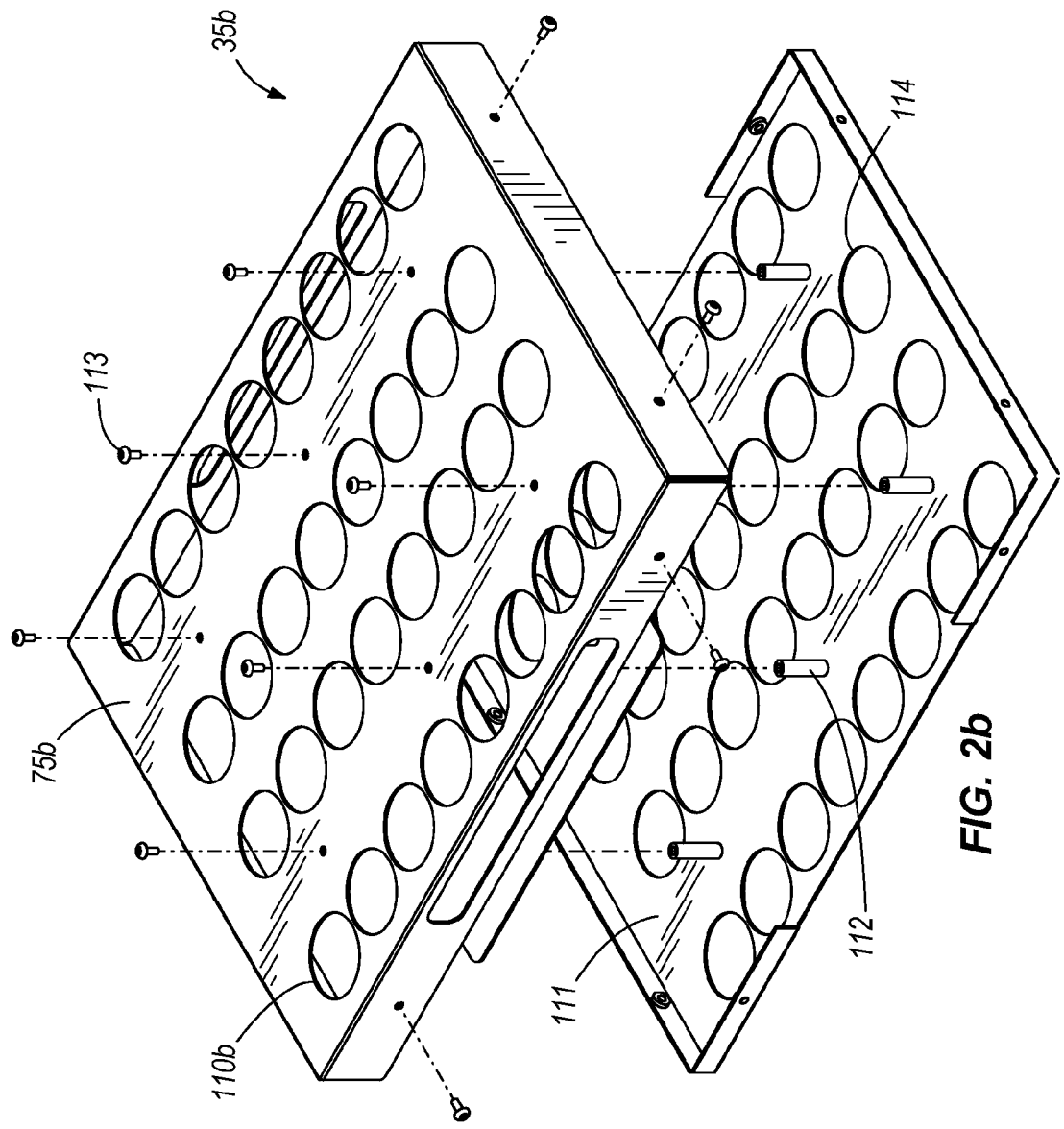
FIG. 2b is an exploded view of an alternative construction of the transport rack of FIG. 2.

FIG. 2b illustrates an alternative construction of a transport rack 35b. A bottom planar member 111 may be positioned below and in parallel to the top surface 75b. A plurality of threaded stand-offs 112 separate the bottom planar member 111 and top surface 75b, while a plurality of threaded fasteners 113 fasten the transport rack 35b together as a rigid, three-dimensional structure. The second planar member 111 has an array 114 similar to, and aligned with, the top surface array 110b. The second planar member 111 serves to capture and align sample tubes as the transport rack 35b is lowered into position on the HSM 10.

As shown in FIG. 1, the HSM 10 includes a housing 115. In the construction shown, portions of the housing 115 are formed from aluminum sheet stock. In other constructions, the housing 115 may include molded plastic or other material. A control panel 120 is fixed to a front surface of the apparatus. The control panel 120 includes a plurality of control buttons 125 for selecting the operating mode of the apparatus 5, and an LED, LCD, or other type of display 130 for displaying parameters such as temperature set points, shaker speed, and magnet position. In the construction shown, four buttons 125 are provided for programming and operating the apparatus 5. An "enter" button executes assigned functions. An "escape" button cancels the practicing function or returns to a previous menu on the display. An "up" button moves a display cursor up or commands ON. A "down" button moves the cursor down or commands OFF. In other constructions, the number and function of the buttons on the control panel 120 may differ or the control panel 120 may be located on another surface of the apparatus 5, or externally for remote control and operation.

A plurality of circular apertures 135 extend through an anti-contamination cover 140 of the HSM 10. The apertures 135 are sized and arranged for receiving a plurality of containers; e.g., the conical sample tubes discussed earlier. The array of apertures 135 of the anti-contamination cover 140 matches the array presented by the transport rack 35, such that the transport rack 35a, 35b with containers may be lowered into corresponding apertures 135 of the HSM 10. The transport rack 35a, 35b is retained on the anti-contamination cover 140 by the edge surfaces 80, 85, 90, 95 of the transport rack 35a, 35b wrapping around the outer perimeter of the anti-contamination cover 140. In addition, the containers carried in the transport rack 35a, 35b serve to align and retain the rack within the anti-contamination cover apertures as the transport rack 35a, 35b is lowered upon the anti-contamination cover 140. In the construction shown in FIGS. 1 and 2a, four captive screws 145 on the transport rack 35a are provided to fasten the transport rack to the anti-contamination cover 140, via four threaded apertures 150 provided in the surface of the anti-contamination cover 140. In some constructions, edge surfaces 80, 85, 90, 95 provide adequate retention of the transport rack 35a to the anti-contamination cover 140 during sample shaking operations, making the captive screws 145 redundant.

Figure 3:
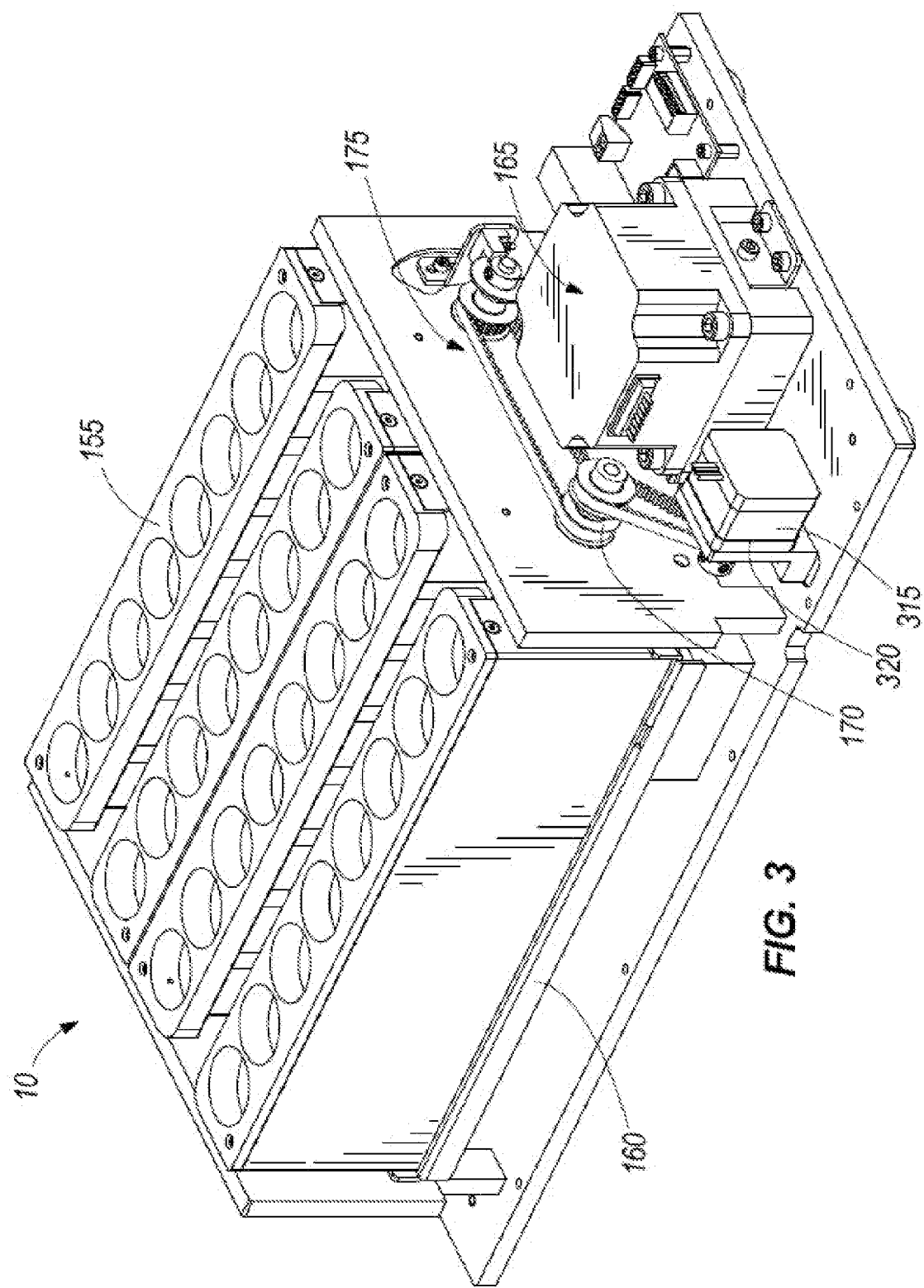
FIG. 3 is a perspective view of a heater/shaker/magnetizer of the apparatus of FIG. 1, with a housing and an anti-contamination cover removed.
Figure 4:
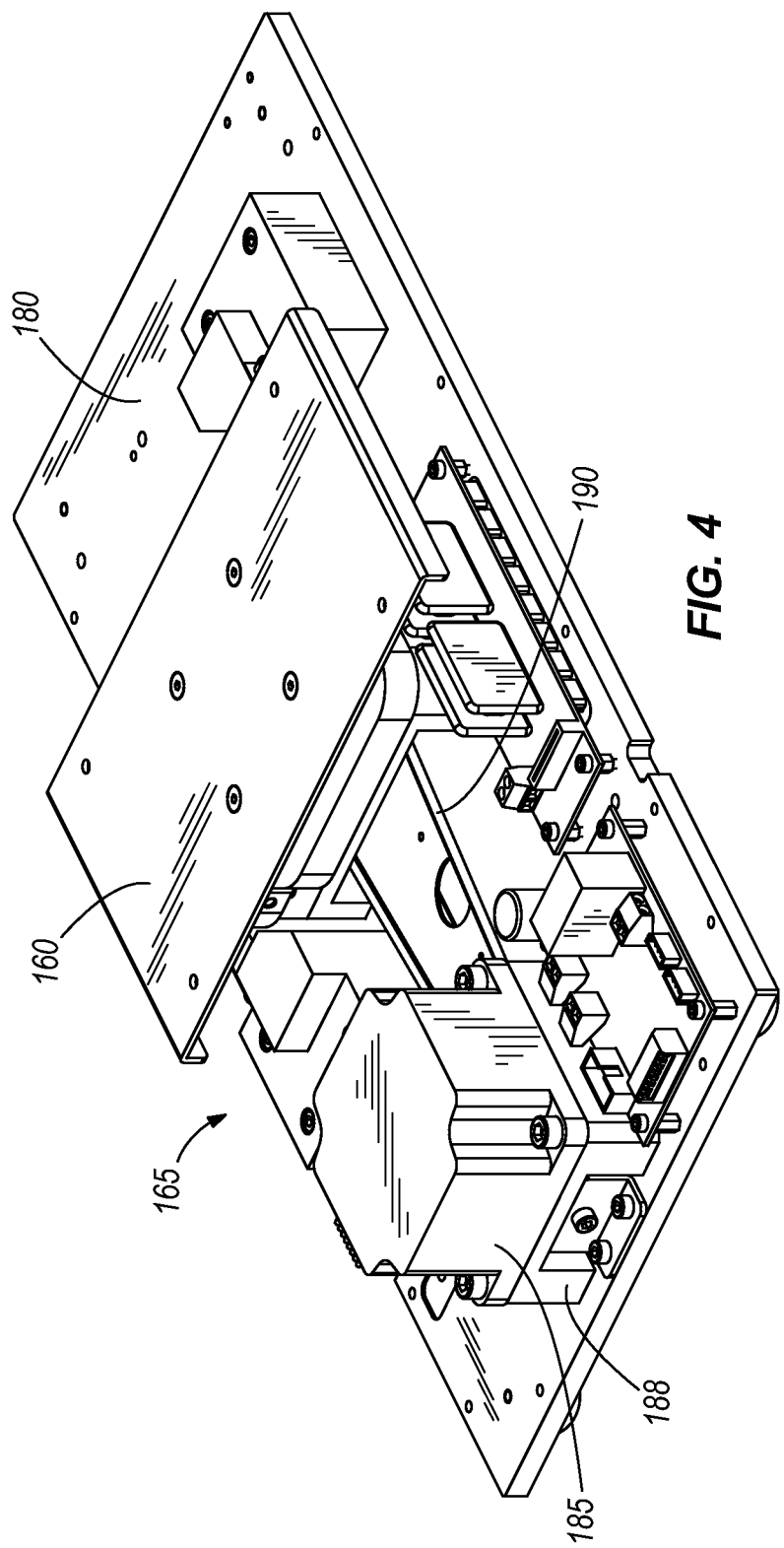
FIG. 4 is a perspective view of a shaker drive assembly of the apparatus of FIG. 1.

FIG. 3 illustrates the HSM 10 with a portion of the housing 115 and anti-contamination cover 140 removed. A plurality of parallel heater blocks 155 are shown, fixedly attached to a shaker platform 160. The shaker platform 160 is driven by shaker drive assembly 165 (FIG. 4). A pair of rotatable magnet assemblies 170 (FIG. 8) is driven by a separate magnet drive assembly 175 with a belt pulley system.

Figure 5:
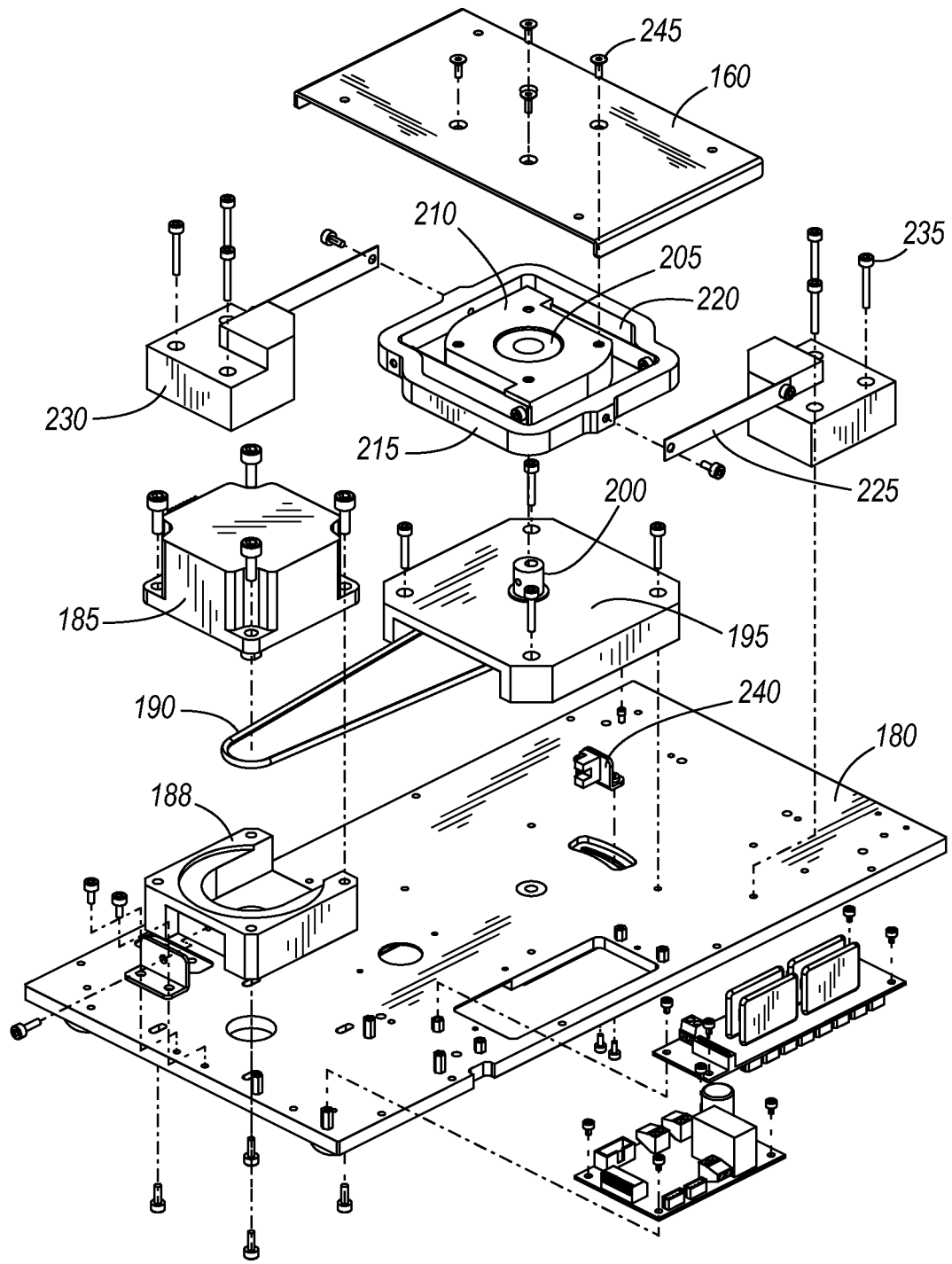
FIG. 5 is an exploded view of the shaker drive assembly of FIG. 4.

FIGS. 4 and 5 illustrate one construction of the shaker drive assembly 165 of the HSM 10. A rigid base plate 180 of the housing 115 provides a stable mounting platform for the subassemblies of the HSM 10. A DC shaker motor 185 is mounted within a shaker motor housing 188. The DC shaker motor 185 may be of various sizes and configurations depending on the desired sample load. In the construction shown, a brushless DC (BLDC) motor is used. The shaker motor shaft is connected via a motor pulley to a shaker drive belt 190. The shaker drive belt 190 wraps around a spindle pulley in a spindle housing 195. The spindle pulley is connected via a shaft to an eccentric cam 200. The cam is generally cylindrical with an off-geometric-center axis of rotation, causing the outer radial surface to have a desired eccentricity while rotating. A cylindrical bearing 205 around the cam 200 bears upon a shaker spindle 210 while rotating, causing the shaker spindle 210 to oscillate in an orbital pattern. The shaker spindle 210 is resiliently mounted to a balancer housing 215 via a first pair of parallel leaf springs 220 on opposing sides of the shaker spindle. The balancer housing 215 is resiliently mounted to the base plate 180 via a second pair of opposing leaf springs 225, the second pair of parallel leaf springs mounted perpendicular to the first pair of leaf springs. The second pair of leaf springs 225 mounts to the base plate 180 via a pair of rigid spring mounts 230, which bolt to the base plate 180 via a plurality of threaded fasteners 235. In the construction shown, three socket head cap screws are used. It should be appreciated that a variety of alternative drive mechanisms are possible. For example, other embodiments may have direct drive of the spindle without the pulleys and belt disclosed herein.

In some constructions, a shaker home position sensor 240 is provided. As described in greater detail below, the home position sensor may be used where the clearances between those components fixed to the movable shaker platform 160 and those components fixed to the base plate 180 are close enough that contact or impact could occur depending on the position of the movable shaker platform 160. In the construction illustrated in FIG. 5, the home position sensor 240 is associated with the spindle pulley. Where a synchronous BLDC motor is used to drive the shaker, a position sensor could also be associated with the motor or a motor controller. The shaker position sensor may also be associated with the motor pulley, the shaker bearing, or the shaker spindle.

Figure 6:
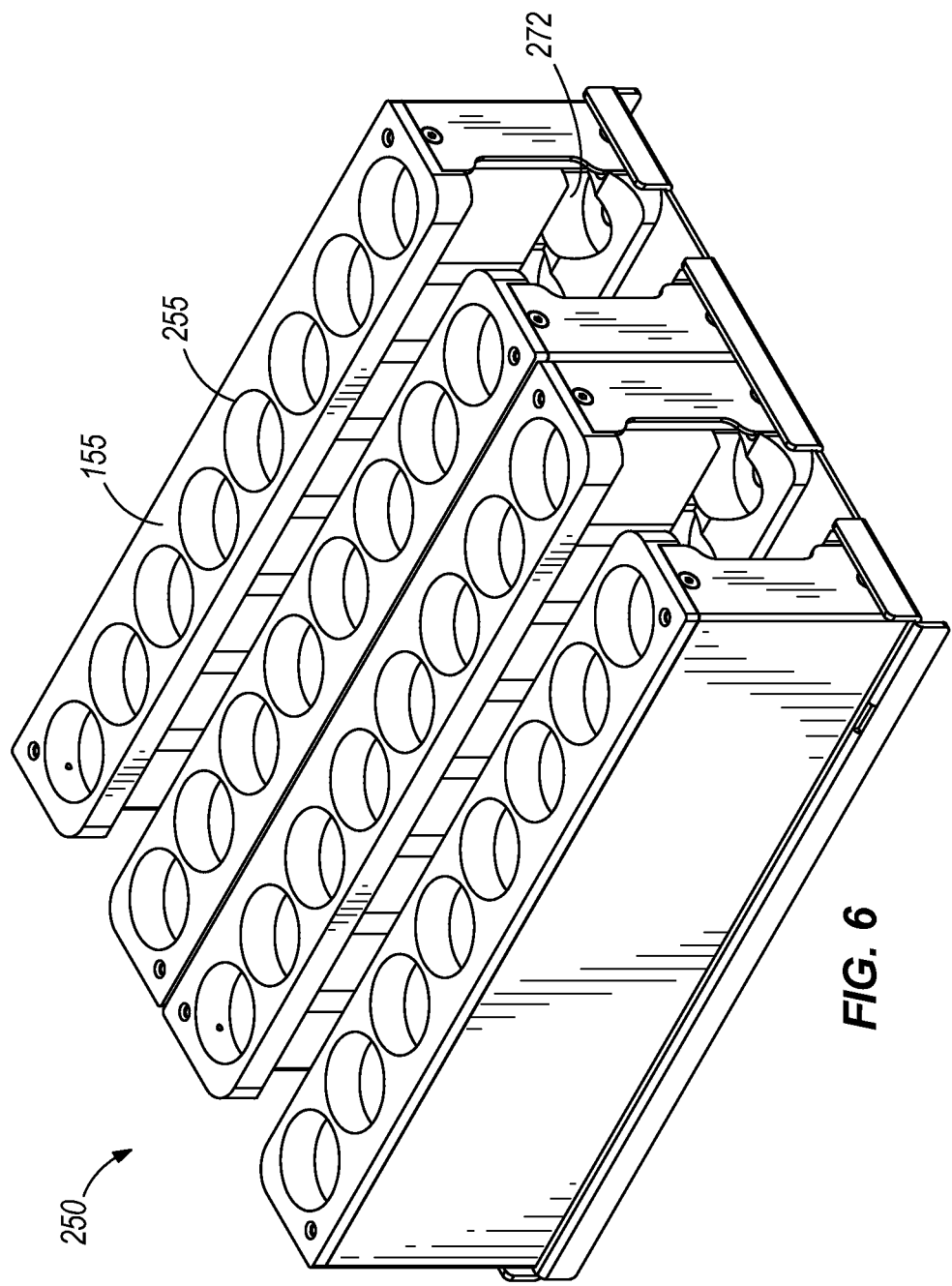
FIG. 6 is a perspective view of a heater block assembly of the apparatus of FIG. 1.

The shaker platform 160 is fixed to the shaker drive assembly 165 via a plurality of threaded fasteners 245. In the construction shown, four socket, flat head machine screws are used. FIG. 6 illustrates the heater block assembly 250, which mounts to the shaker platform 160 (i.e., the shaker platform 160 supports the heater block assembly 250) via a plurality of threaded fasteners. The heater block assembly 250 is composed of a plurality of parallel heater blocks 155. In the construction shown, the heater block assembly 250 includes four heater blocks 155, each heater block 155 having eight apertures 255 for receiving respective containers, thereby resulting in thirty-two apertures 255. In other constructions, various configurations of heater blocks and heater block assemblies could be used. For example, it may be desirable to have a HSM for smaller-scale processing that has two heater blocks for a total of sixteen samples, or it may be desirable to have six or eight heater blocks for larger scale processing.

Figure 7:
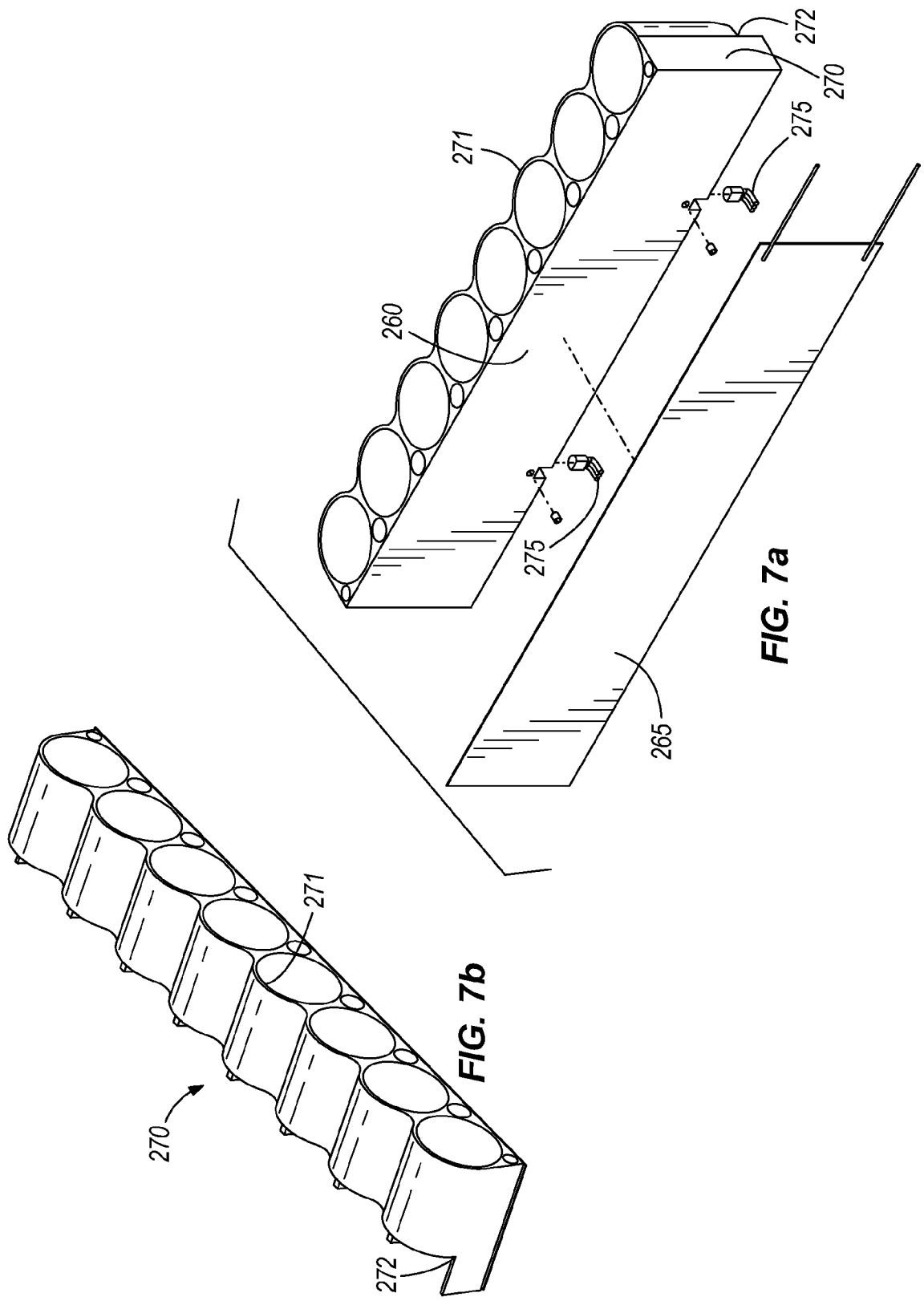

As illustrated in FIG. 7a, on a vertical surface 260 of each heater block 155, a thin film-type resistive heater 265 is adhesively applied to provide a heat flux to the sample tubes while processing them. The resistive heater 265 may be selectively energized alone, or while shaking or magnetizing samples, depending on the desired parameters. In the construction shown, the resistive heater 265 is applied to an aluminum core 270 of the heater block 155 in order to maximize heat transfer from the heater to the sample tube. The aluminum core 270 provides maximum contact around the circumference of the containers held therein, thus promoting conductive heat transfer from the heater 265 to the containers, while having sufficient clearance to allow the containers to be easily inserted or removed. The walls 271 of the aluminum core 270 have a thin cross section in order to minimize the thermal response time once the heater 265 is energized and to maximize the available space between the heater blocks 155. With reference to FIGS. 6 and 7b, and described in greater detail below, a bottom portion 272 of the aluminum core 270 is cutaway to provide a minimum clearance for the magnet assemblies 170. In the construction shown, the other major portions of the heater block are machined from a rigid polymer such as DuPont Delrin™ or the like. In some constructions, one or more temperature-sensing thermocouples 275 may be associated with each resistive heater 265. The thermocouples, in combination with the resistive heaters 265, allow for the programming of temperature set points within the heater blocks. In the construction shown, two thermocouples 275 are associated with each heater 265.

As illustrated in FIG. 3, one or more magnet assemblies 170 and a magnet drive assembly 175 are affixed to the base platform 180. The magnetic assemblies 170 and magnetic drive assembly 175 selectively applying a magnetic field to magnetic, or paramagnetic, particles, which may be present in some samples within the containers. As an example, MagneSil™ Paramagnetic Particles (PMPs) use the principle of magnetic separation as an alternative to vacuum filtration and centrifugation separation formats. There are numerous purification applications for MagneSil™ PMPs in the life sciences and in industrial laboratories. Magnetic particles can be considered a "mobile solid phase" within a liquid sample. The particles consist of a nearly 1:1 ratio of silicon dioxide ($SiO_2$) to magnetite. The high magnetite concentration makes the particles responsive to a magnetic field. However, the particles are paramagnetic in that they are attracted to the magnetic field of an external magnet, but will not remain magnetized when removed from the magnetic field. The silicon dioxide ($SiO_2$) matrix allows for a binding capacity with nucleic acids. The application of a magnetic field to the sample, after the binding of nucleic acids, separates the PMPs and attached nucleic acids from the remainder of the solution. With the magnetic field applied, an external pipette can withdraw a portion of the solution, thus increasing the concentration of nucleic acids within the sample. This description of one application for the magnetizing portion is exemplary. In some applications, a cellulose-based PMP may be preferable to MagneSil™ PMPs. Furthermore, persons skilled in a variety of industrial and scientific arts will recognize the value of selective magnetizing capability in an apparatus also capable of shaking and heating functions.

Figure 8:
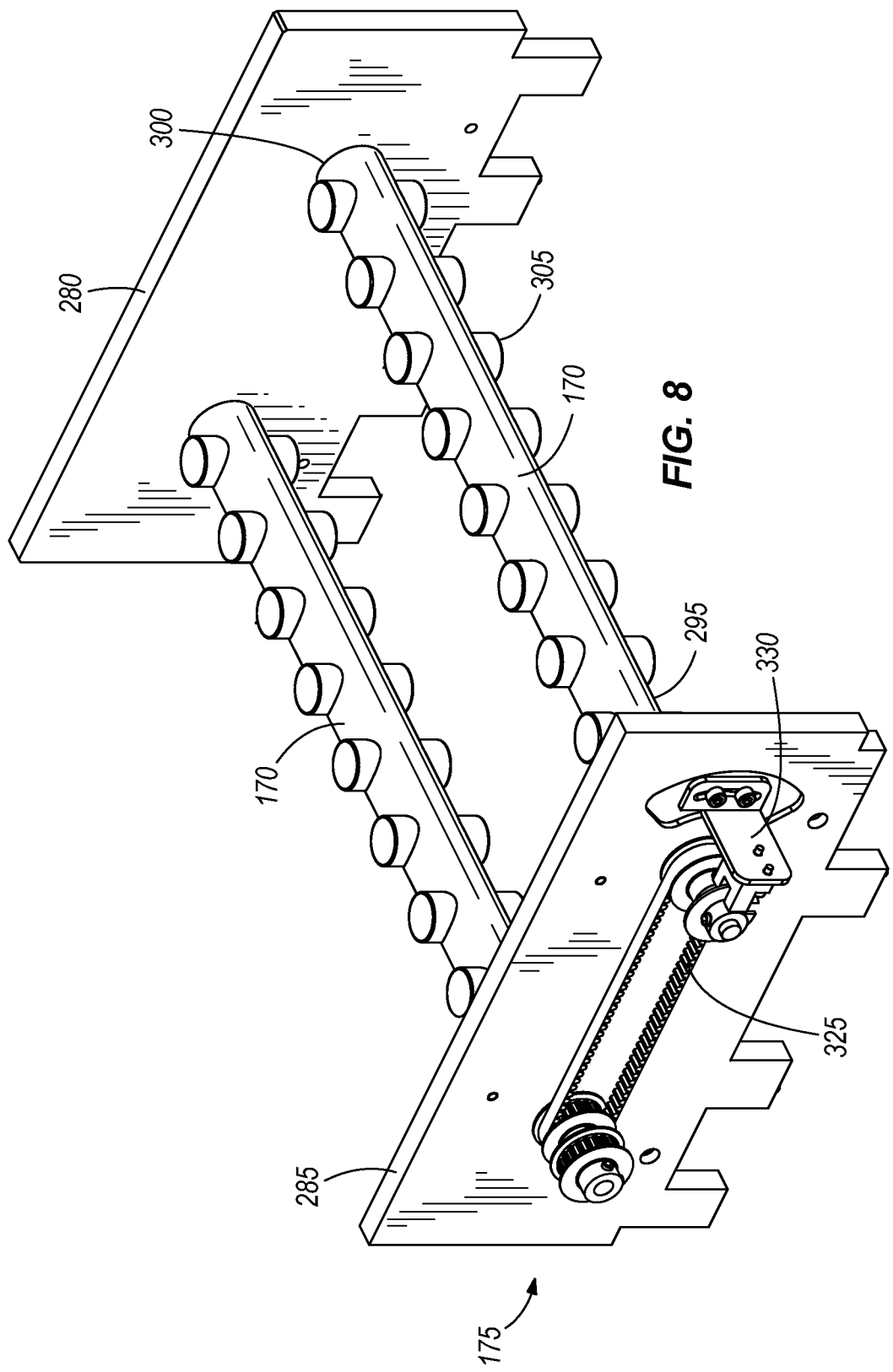
FIG. 8 is a perspective view of a magnet drive assembly of the apparatus of FIG. 1.
Figure 9:
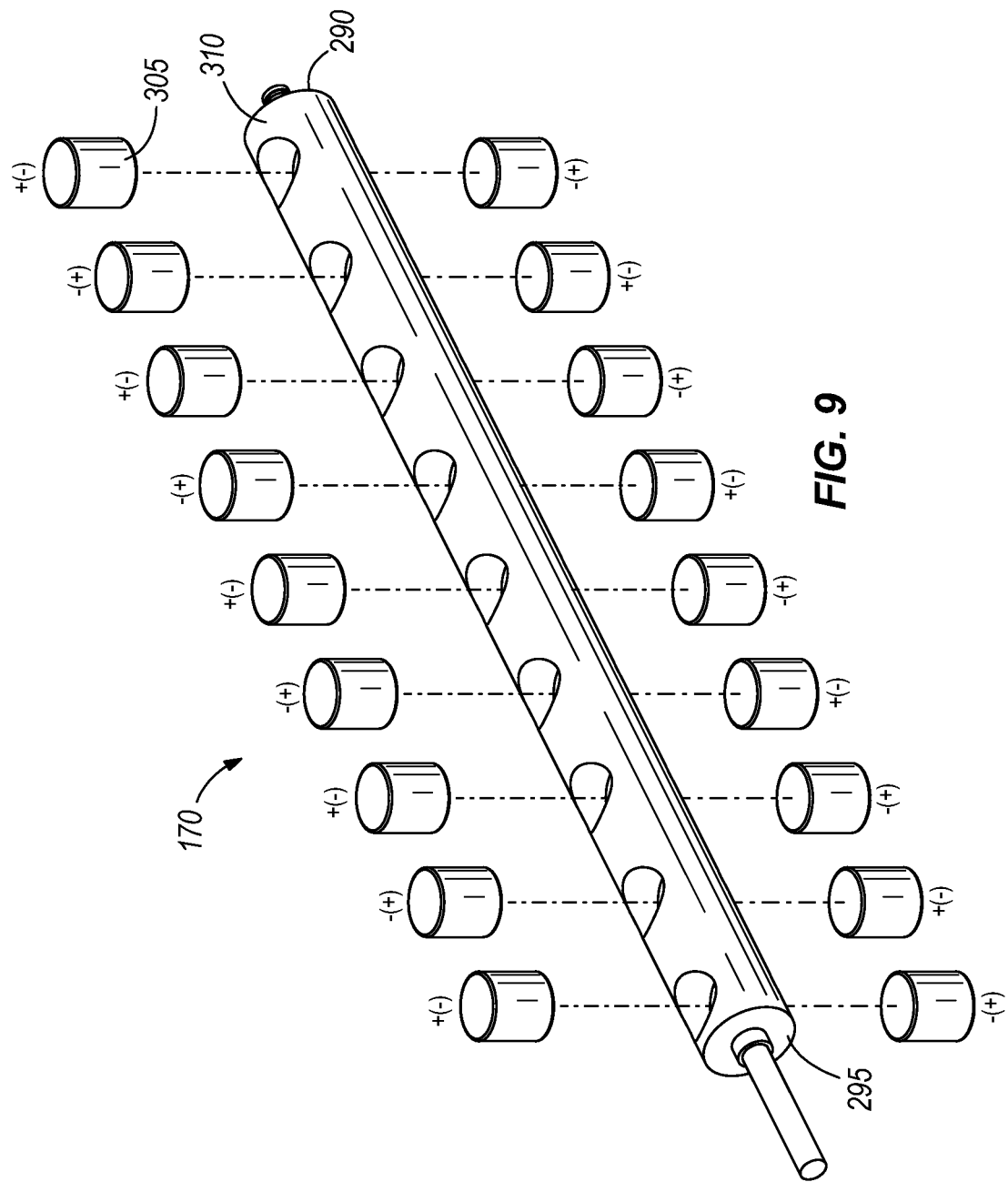
FIG. 9 is an exploded view of one magnet assembly of the magnet drive assembly of FIG. 9.

With reference to FIGS. 8 and 9, the magnet drive assembly 175 includes front and back mounting plates 280, 285, rigidly fastened to the base plate 180 (FIG. 3). Cylindrical magnet assemblies 170 rotate at first and second ends 290, 295 (FIG. 9) within bearing apertures 300 of the front and back mounting plates. Because the magnet assemblies 170 are pivotally fixed to the base plate 180 (via the front and back mounting plates 280, 285), they are independent of the motion of the shaker platform 160. Each of the cylindrical magnet assemblies 170 has a plurality of radially-opposed permanent magnets 305 affixed in radial bores of a cylindrical magnet holder 310. In the embodiment shown, a total of eighteen permanent magnets 305 are affixed to each magnet assembly 170 in two opposing rows of nine magnets. The opposing rows are approximately 180 degrees apart. The magnets 305 may be permanent magnets or electro-magnets. In the construction shown, rare earth permanent magnets are used for their high magnetic field strength to volume ratio. In the construction shown, two cylindrical magnet assemblies 170 are provided, though in other embodiments, a single magnet assembly could be used between two racks, or three or more magnet assemblies could be used where greater than four racks are used.

As illustrated in FIG. 9, the magnets 305 are arranged such that the poles of radially opposed magnets on each magnet holder 310 are attracted to each other. In other words, the positive pole of the magnet on one radial side of the magnet holder 310 faces a negative pole of the magnet in the opposite radial position the magnet holder. Such an arrangement aids in retaining the opposing magnets within the magnet holder. In the construction shown, the polarity sequence of adjacent magnets in each row alternates with every magnet in the row (+, −, +, −, +, etc.). Such an arrangement produces adequate field strength while allowing the magnet assemblies to be rotated with relatively low torque. In other constructions, however, it may be preferable to have adjacent magnets in each row with matching polarity.

Figure 10A:
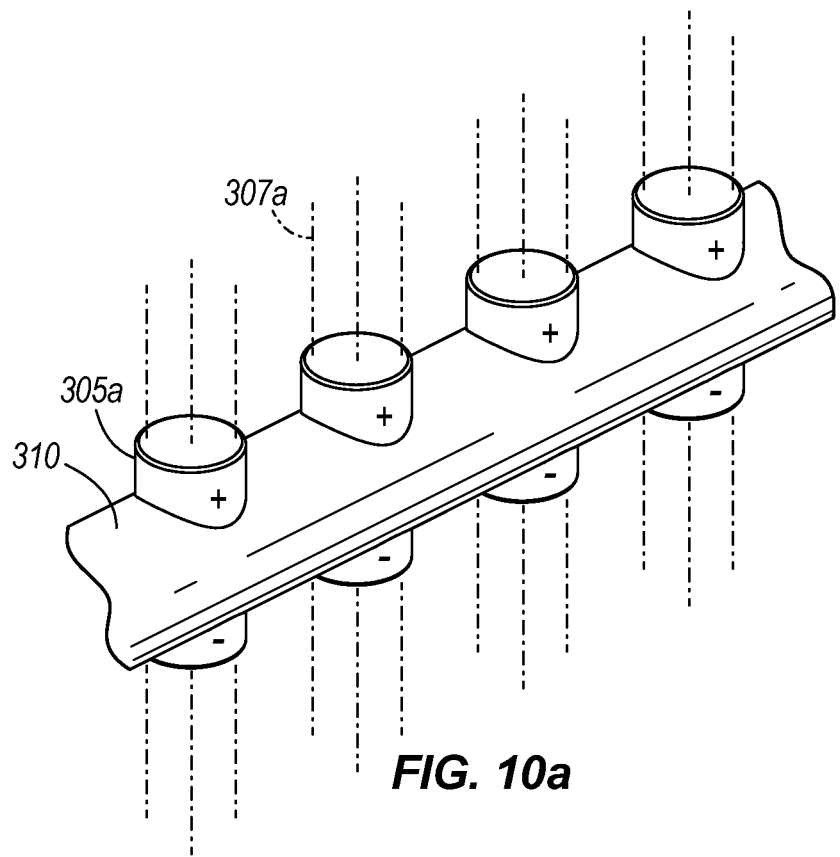
FIG. 10a is a perspective view of a magnetic field of one embodiment of the magnet assembly of FIG. 9.
Figure 10B:
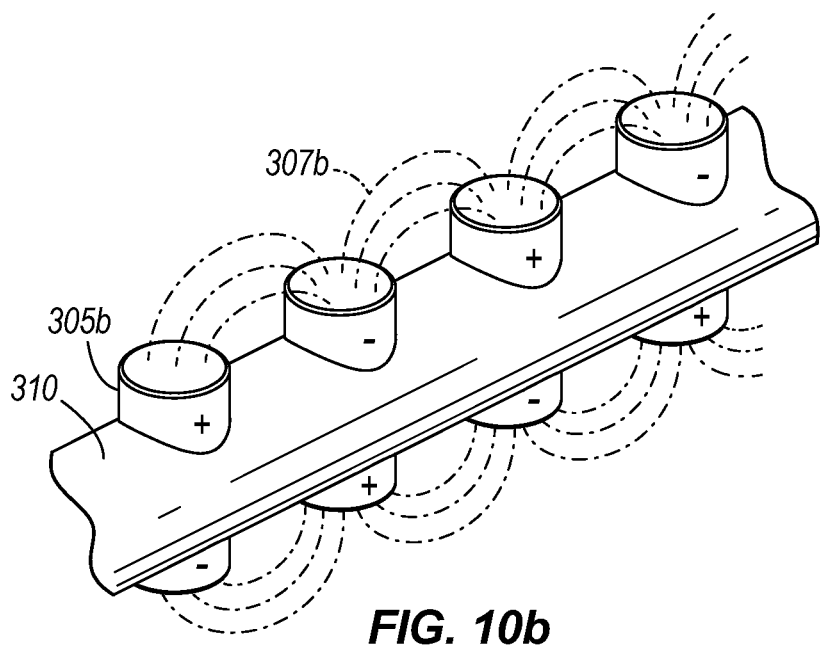
FIG. 10b is a perspective view of a magnetic field of another embodiment of the magnet assembly of FIG. 9.

The magnet assembly 170 shown in FIG. 9 is exemplary and it should be recognized that other configurations of magnets are possible. The design and arrangement of the magnets 305 can vary the magnetic fields among multiple designs, thereby allowing a designer to tailor the magnetic field to an application. For example, as shown in FIG. 10a, utilizing matching polarities with adjacent magnets 305a provides a different magnetic field than utilizing non-matching polarities with adjacent magnets 305b, as shown in FIG. 10b. For FIG. 10a, the magnetic field 307a is more consistent along an axis of the holder 310 than the magnetic field 307b of FIG. 10b.

Referring again to FIGS. 3 and 8, a magnet drive assembly 175 is provided for selectively rotating the magnet assemblies 170 from a first position to a second position. In the first position, shown in FIG. 8, the magnets 305 are oriented in a vertical plane. The magnetic field produced by the magnets 305 in the first position has substantially no effect on the samples. In the second position, the magnets 305 on each magnet assembly 175 are oriented in a horizontal plane. In the second position, the ends of each magnet are brought in close proximity to the samples within the containers held within the heater blocks 155. The magnetic field produced by the magnets, when in the second position, is applied to the samples for various uses. The magnets on each magnet assembly 170 are axially spaced such that with nine magnets per side of each magnet assembly, each container held within an eight-container heater rack is adjacent to two magnets. In other embodiments, it is not necessary to position two magnets 305 adjacent to each container. One magnet, or multiple magnets may be positioned adjacent to each container to provide higher, lower, more diffuse or more focused magnetic fields. The magnet drive assembly 175 uses a stepper motor 315 (FIG. 3) supported by a motor housing 320 to drive a belt/pulley assembly 325. The belt/pulley assembly 325 in the construction shown operates both magnet assemblies in unison. In constructions where mechanical interference or impact is possible between the magnet assemblies, in certain positions, and the shaker assembly, a magnet home position sensor 330 mounted to the back plate 285 is operable to indicate whether the magnet assemblies 170 are in the first position or second position. In the construction shown, the magnet home position sensor 330 is substantially similar to the shaker home position sensor 240, and is similarly associated with a pulley.

In other constructions, it is desirable to operate the magnet assemblies 170 independently via a plurality of drive assemblies, or a plurality of direct-drive stepper motors. In still other constructions, the magnet assemblies 170 are manually positioned by a user via an external knob or the like. Variations on the orientation of the magnet assemblies 170 are also possible. For example, a plurality of magnets 305 could be raised or lowered with respect to the containers from a position within the HSM 10.

By having the combination of a shaking portion (e.g., the shaker drive assembly 165), a heating portion (e.g., the heater block assembly 250), and a magnetizing portion (e.g., the magnet assemblies 170), the HSM 10 offers the ability to selectively heat, shake, and apply a magnetic field to a plurality of samples without the need to move the samples to separate stations. The sequence of modes and settings depends upon the type of sample and the specific parameters required for processing. While all constructions of the HSM 10 have the ability to heat, shake, and magnetize in a serial sequence, some constructions may allow for simultaneous heating, shaking, and/or magnetizing. For example, it may be desirable in certain applications to apply a heat flux from the resistive heaters 265, while shaking the sample, or while applying the magnetic field. It should be noted, however, that the combination of shaking and magnetizing may be undesirable in many processes.

Furthermore, in some constructions there may be mechanical interference between the magnet assemblies 170 and the shaker assembly 165 (and attached heater block assembly 250) when one or both are in certain positions. In these constructions, the shaker home position sensor 240 and the magnet home position sensor 330 are necessary to prevent conditions of interference. In the construction shown in FIG. 3, for example, the shaker motor 185 cannot be operated unless the magnet assemblies are oriented in the home (first) position as indicated by the magnet home position sensor 330. Similarly, the magnet assemblies 170 cannot be rotated by the stepper motor 315 from the first position to the second position unless the shaker motor 185 is stopped and the shaker drive assembly 165 is oriented in the home position, as indicated by the shaker home position sensor 240. With the shaker drive assembly 165 in the home position, the cutaway bottom portion 272 of the aluminum core 270 provides sufficient clearance to rotate the magnet assemblies 170 from the first position to the second position and from the second position back to the first position. Having both a shaker home position sensor 240 and a magnet home position sensor 330 provides, in at least one construction, additional advantages. Ensuring maximum horizontal clearance when the magnet assemblies 170 are oriented in the home position allows for a larger orbital shaking motion of the shaker assembly 165. The shaker home position sensors 240 allows for the magnet assemblies 170, in the second position, to be in close proximity with the containers for a strong magnetic field applied to the samples. The homing capabilities of both the shaker drive assembly 165 and the magnet assemblies 170 facilitates a highly reproducible step-to-step and run-to-run relationship between magnets and containers, ensuring a greater degree of repeatability in magnetic field strength applied to the samples, resulting in more consistent processing. This may be advantageous in certain constructions given the inverse square relationship between magnetic field strength and distance.

Figure 11:
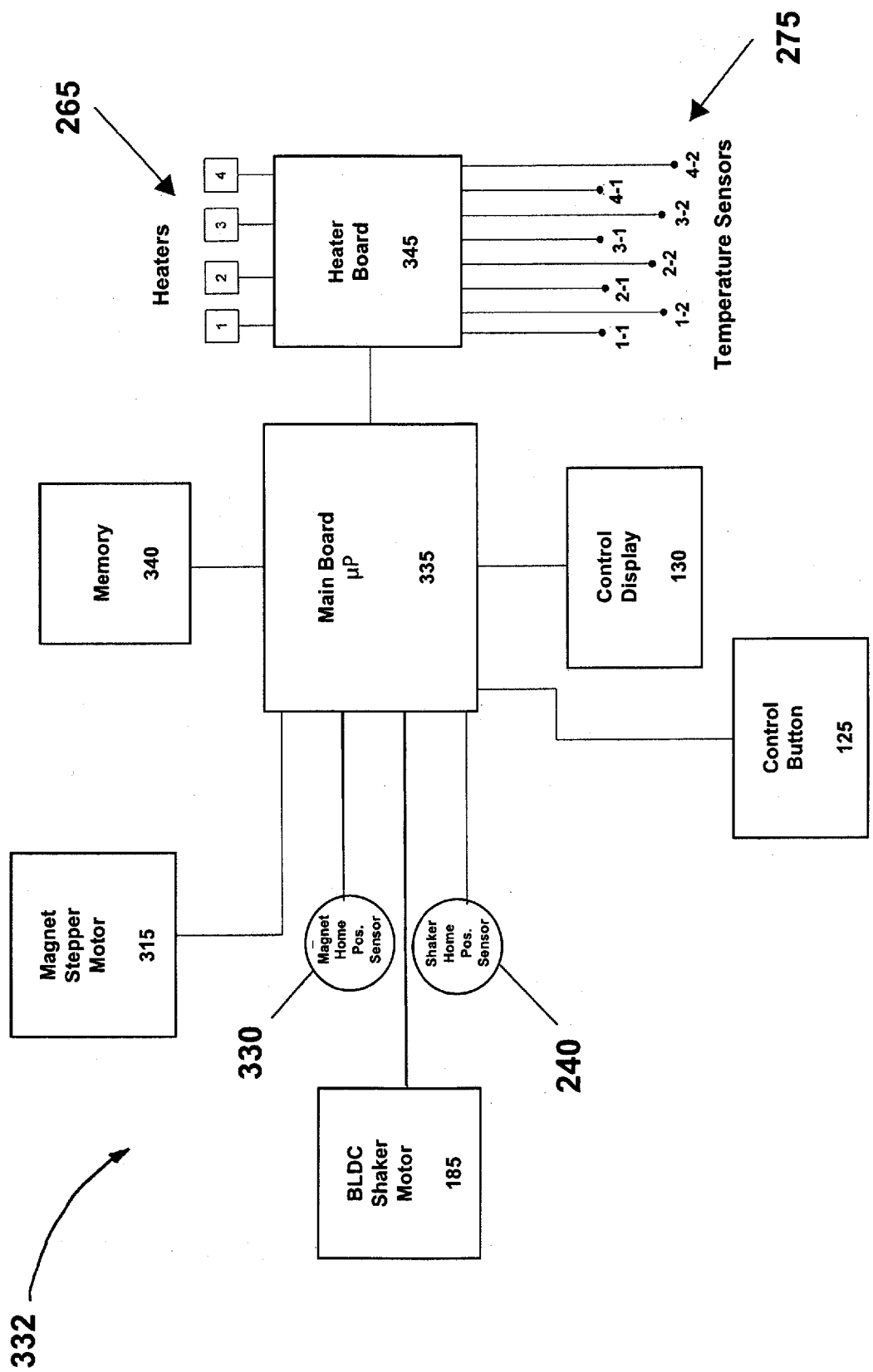
FIG. 11 is a functional block diagram of a control circuit of the apparatus of FIG. 1.

FIG. 11 illustrates a block diagram of a control circuit 332 for the HSM 10, including associated sensor inputs. A main board 335 contains a microprocessor. A memory unit 340 associated with the main board stores executable instructions and data, such as set points and various operating parameters. The main board 335 is operable to control operation of the shaker motor 185 and magnet stepper motor 315, but typically upon conditions established by signals from the associated magnet home position sensor 330 and shaker home position sensor 240. Similarly, the main board 335 receives heater block temperature data from each of the two thermocouples 275 associated with each heater block 155. A heater board 345 provides signal conditioning between the thermocouples 275 and the main board 335. By comparing the sensed temperature with a set-point stored in the memory unit 340, the main board 335 is operable to selectively energize each of the resistive heaters 265.

Thus, the invention provides, among other things, an apparatus for processing liquid samples. Various features and advantages of the invention are set forth in the following claims.

What is claimed is:

1. An apparatus for processing a liquid sample in a sample tube, comprising
a base;
a receptacle for receiving a sample tube;
a heating portion coupled to the base to selectively apply heat to the receptacle;
a shaking portion coupled to the base and supporting the receptacle, the shaking portion agitating the receptacle with respect to the base; and
a magnetizing portion coupled to the base and movable to selectively change a magnetic field with respect to the receptacle, wherein the magnetizing portion comprises
a first magnet holder having a first axis, the first magnet holder rotatably coupled to the base for rotation about the first axis,
a first plurality of magnets fixedly coupled to the first magnet holder, and
a magnet drive mechanism selectively driving the first magnet holder between a first axial orientation and a second axial orientation.

2. The apparatus of claim 1, wherein the heating portion comprises a resistive heater.

3. The apparatus of claim 1, wherein the heating portion is coupled to the shaking portion for movement with the shaking portion.

4. The apparatus of claim 1, wherein the heating portion is coupled to the receptacle.

5. The apparatus of claim 4, wherein the heating portion comprises a resistive film heater.

6. The apparatus of claim 1, wherein the shaking portion is operable to rotate the receptacle with respect to the base in an orbital motion.

7. The apparatus of claim 1, wherein the first plurality of magnets are arranged with magnetic poles oriented substantially perpendicular to the first axis.

8. The apparatus of claim 7, wherein adjacent magnets of the first plurality of magnets have a substantially similar polar orientation.

9. The apparatus of claim 7, wherein adjacent magnets of the first plurality of magnets have substantially opposed polar orientations.

10. The apparatus of claim 1, wherein the magnetizing portion further comprises
a second magnet holder having a second axis, the second magnet holder rotatably coupled to the base for rotation about the second axis, and
a second plurality of magnets fixedly coupled to the second magnet holder, the magnet drive mechanism selectively driving the second magnet holder between a third axial orientation and a fourth axial orientation.

11. The apparatus of claim 1, wherein the receptacle includes an aperture for receiving the magnetizing portion.

12. A sample processing apparatus comprising:
a base;
a platform coupled to the base for motion with respect to the base;
a platform drive assembly including a platform drive motor coupled to the base and an orbital drive coupled to the platform;
a receptacle fixedly coupled to the platform, the receptacle receiving a sample tube and including a heating portion for selectively applying a heat to the sample tube;
a magnetizing portion movably coupled to the base, the magnetizing portion including a permanent magnet having a first magnetic field orientation with respect to the receptacle and a second magnetic field orientation with respect to the receptacle;
a magnet drive assembly coupled to the base and the magnetizing portion for moving the permanent magnet between the first magnetic field orientation and the second magnetic field orientation, and
a controller for selectively controlling the platform drive assembly, heating portion, and magnet drive assembly, the controller including logic to prevent operation of the magnet drive assembly during operation of the platform drive motor.

13. The sample processing apparatus of claim 12, wherein the magnet drive assembly includes a stepper motor.

14. The sample processing apparatus of claim 12, further comprising a magnet position sensor for measuring a position of the magnet.

15. The sample processing apparatus of claim 14, further comprising a platform position sensor for measuring a position of the platform relative to the base.

16. An apparatus for selectively heating, shaking, and magnetizing a plurality of sample tubes, comprising;
a base member;
a drive assembly including a drive motor and an orbital shaker assembly coupled to the drive motor;
a heater block assembly coupled to the orbital shaker assembly for orbital motion with respect to the base member, the heater block assembly comprising
a heater block having a plurality of apertures, each aperture for receiving a sample tube, and
an electric heater thermally coupled to the heater block for applying a heat to the sample tubes;
a magnet assembly including a magnet having a magnetic field and a drive coupled to the base for moving the magnet between a first magnetic field orientation and a second magnetic field orientation;
a controller for selectively energizing the electric heater, selectively operating the drive assembly, and selectively moving the magnet between the first magnetic field orientation and the second magnetic field orientation, and
a magnet position sensor for measuring a position of the magnet relative to the base and generating a first signal, the controller receiving the first signal and selectively operating the drive assembly based in part upon the first signal.

17. The apparatus of claim 16, further comprising an orbital shaker position sensor for measuring a position of the orbital shaker relative to the base and generating a second signal, the controller receiving the second signal and selectively operating the magnet drive based in part upon the second signal.

* * * * *